United States Patent [19]

Salisbury

[11] 4,421,618
[45] Dec. 20, 1983

[54] PHOTOISOMERIZATION OF TRANS-CYCLOPROPANE-NITRILES

[75] Inventor: Kingsley Salisbury, Sittingbourne, United Kingdom

[73] Assignee: Shell Internationale Research Maatschappij B. V., The Hague, Netherlands

[21] Appl. No.: 396,428

[22] Filed: Jul. 8, 1982

[30] Foreign Application Priority Data

Jul. 22, 1981 [GB] United Kingdom ................. 8122651

[51] Int. Cl.$^3$ .............................................. B01J 19/12
[52] U.S. Cl. ................................................ 204/158 R
[58] Field of Search ........................ 204/158 N, 158 R

[56] References Cited

U.S. PATENT DOCUMENTS 3,496,080  2/1970  Harris ............................ 204/158 R

FOREIGN PATENT DOCUMENTS 1491408  11/1977  United Kingdom .

OTHER PUBLICATIONS

J.C.S. Perkins, 1980, pp. 728 through 732.

Primary Examiner—Howard S. Williams
Attorney, Agent, or Firm—Pravel, Gambrell, Hewitt, Kirk & Kimball

[57] ABSTRACT

Trans-cyclopropane-nitriles of the following general formula:

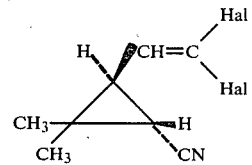

can be converted into the corresponding cis-form by irradiating the trans-compound with light of wavelength in the range 260–450 nanometers in the presence of a photo-sensitizer the triplet state energy of which is in the range 220–230 kilojoules per mole.

9 Claims, No Drawings

PHOTOISOMERIZATION OF TRANS-CYCLOPROPANE-NITRILES

This invention relates to a process for the photoisomerisation of trans-cyclopropane-nitriles into their corresponding cis-form.

Pyrethroid insecticides many of which are based on cyclopropanecarboxylates for example, permethrin, cypermethrin and decamethrin, are now established as important products in the agrochemical industry. A number of cyclopropane carboxylates can exist in cis- and trans-forms and generally it has been found that the cis-form is more pesticidally-active than the corresponding trans-form so that any method of converting trans-cyclopropanecarboxylates into the cis-form is a valuable and useful development.

It is known from J. C. S. Perkin I 1980, 728–732 that photoisomerisation of methyl cis-2,2-dimethyl-3-(2,2-dihalovinyl)-cyclopropanecarboxylate can be achieved (i.e. the cis-form can be converted to the trans-form) but that it occurs with substantial re-arrangement and decomposition of the irradiated product.

It is also known from UK No. 1,491,408 that trans-2-2,2-di-chlorovinyl)-3,3-dimethylcyclopropanecarboxylic acid or its methyl ester can be converted into the corresponding cis-form by irradiation with ultra-violet rays in the presence of a photosensitizer. The maximum conversion recorded in UK No. 1,491,408 is a 40% conversion of trans- to cis -ismoers; it can be expected from basic stero-chemical considerations that the trans-isomer will be more stable than the cis-isomer and that therefore a 50% conversion trans to cis is the maximum conversion that is likely to occur in practice.

However, the Applicant has found that with 2,2-dimethyl-3-(2,2-dihalovinyl)-cyclopropane-nitrile the trans-form can be converted into the corresponding cis-form at conversions of greater than 50% and in the substantial absence of rearrangement or of decomposition products by irradiation with light within a defined wavelength range in the presence of specific photosensitizers.

Accordingly, the present invention provides a process for the conversion of a trans-cyclopropane-nitrile of the following general formula

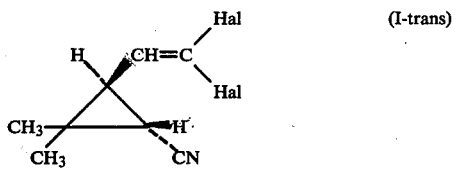

(I-trans)

to the corresponding cis-compound (I-cis), wherein each Hal is a halogen atom, which comprises irradiating the trans-compound (I-trans) with light of wave-length in the range 260–450 nanometers in the presence of a photo-sensitizer the triplet state energy of which is in the range 220–330 kilojoules per mole.

The halogen atom which Hal represents in the general formula depicted above may be fluorine, chlorine, bromine or iodine, but preferably represents chlorine or bromine because active pyrethroid insecticides such as permethrin, cypermethrin and decamethrin are based on cyclopropane-acids derivable from dichlorovinyl or dibromovinyl-cyclopropane-nitriles.

The process according to the invention is useful for converting trans-cyclopropane-nitriles into cis-cyclopropane-nitriles and is especially useful because of the high yields of cis-isomer which can be achieved. Conversions of as high as 60% or more can be realised by this process which is very surprising in view of general stereochemical considerations and in view of the teachings of the prior art, especially UK No. 1,491,408, which suggests that conversions of 40% are as high as can be achieved in practice. Generally speaking, i.e. where both halogen atoms are identical, the racemic form of the dihalovinyl-cyclopropane-nitrile consists of four isomers, the (1R,cis)-, (1S,cis)-, (1R,trans)- and (1S,trans)-isomers and the process according to the invention can be used to convert the two trans-isomers into the two cis-isomers; it can also be used to convert one or both trans-isomers when admixed with varying proportions of one or both cis-isomers.

The nomenclature used in this specification to denote the stereochemistry of the isomers of the dihalovinyl-cyclopropane-nitriles is the so-caled Elliott nomenclature as given in M. Elliott, A. W. Farnham, N. F. Janes, P. H. Needham and D. A. Pulman, Nature, 1974, 248, 710.

Any light source which emits light at a wave-length in the range 260–450 nanometers is suitable, for example a medium or high pressure mercury lamp or a xenon lamp. Preferably the wavelength is in the range 280–400 nanometers. If desired, the light source may have a filter incorporated therein to restrict the light to wavelengths in the range specified above, in other words a filter can be used to protect the cyclopropane-nitrile from harmful radiation outside the desired wavelengths.

The photo-sensitizer used in the process according to the invention must have a triplet state energy in the range 220 to 330 kilojoules per mole but is preferably in the range 250 to 310 kilojoules per mole. Examples of useful sensitizers are diaryl ketones or alkyl aryl ketones such as substituted or unsubstituted phenyl-ketones or substituted or unsubsituted $C_{1-6}$ alkylphenyl-ketones. The preferred sensitizers are acetophenone, propiophenone, n-butyrophenone, isobutyrophenone, and benzophenone which have triplet state energy values of 305, 303, 302, 302 and 289 kilojoules per mole respectively.

"Triplet state energy" is defined as the energy difference between the electronic ground state of a molecule and the first excited triplet state of that molecule. The photosensitizer and the cyclopropane-nitrile are preferably in a homogeneous liquid phase to optimise the efficiency of the photoisomerisation. The nitrile is a low melting point solid and is usually soluble in the photosensitizer which is generally a liquid. Where it is insoluble or the photo-sensitizer is a solid, a solvent can be employed provided that it is photolytically stable and will not react with the sensitizer or the nitrile. Alcohols such as ethanol are suitable solvents.

The amount of photo-sensitizer required to be present in the nitrile depends of course on the nature of the sensitizer but, generally speaking is present in an amount in the range 5–40% by weight of the nitrile, preferably in the range 10–30% by weight.

The process according to the invention is preferably carried out in the absence of oxygen so that photoxidation processes are minimised or eliminated and this can be achieved in practice by performing the photoisomerisation in the presence of an inert gas such as nitrogen.

The process according to the invention is further illustrated by the following Examples, in which the composition of the starting materials and photoisomerised mixtures was measured by glc analysis. The photoisomerisation apparatus employed consisted essentially of a light source (100 watt semi-circular medium pressure mercury lamp or 400 watt cylindrical immersion lamp with an emission profile typical of larger mercury lamps), a quartz cell provided with means to deoxygenate the cell and to introduce a nitrogen blanket over the solution to be isomerised, a cell holder of the type in standard uv/visible spectrometers, and a filter to cut off the light at wave-lengths above 280 nanometers.

EXAMPLES 1 to 5

Conversion of trans-2-(2,2-dichlorovinyl)-3,3-dimethylcyclopropane-nitrile(trans-DCVN) into the corresponding cis-form (cis-DCVN)

Trans-DCVN (containing 1.4% cis-DCVN, m.p. 49°–53° C.) together with a photo-sensitizer was introduced into the cell, and the mixture deoxygenated by purging with nitrogen for 15 minutes. The cell was sealed with a cap which permitted samples to be withdrawn fron the cell for analysis purposes. The cell contained 0.4 g when a 100 watt lamp was used and 0.6 g when a 400 watt lamp was used. Irradiation of the cell then took place and measurements . were taken after 15 hours and at the photostationary state.

A series of experiments were carried out with a range of photo-sensitizers and the results in terms of the analysis after 15 hours irradiation and at the photostationary state are given in Table I.

TABLE I

| Example | Sensitizer (% w/w) | Analysis after 15 hours Irradiation | | | Yield of cis-DCVN at Photo-stationary state |
|---|---|---|---|---|---|
| | | % cis-DCVN | % loss DCVN | % loss sensitizer | |
| 1[a] | acetophenone (40%) | 42.0 | 3.0 | 2.0 | 63 |
| 2[a] | propiophenone (40%) | 37.0 | 0.0 | 0.0 | 62.5 |
| 3[b] | n-butyrophenone (10%) | 45.0 | 7.0 | 7.0 | 61.0 |
| 4[b] | iso-butyrophenone (10%) | 52.0 | 0.0 | 0.0 | 62.0 |
| 5[a] | benzophenone (40%) | 40.0 | 2.0 | 2.0 | 62.5 |

[a]= cell containing 0.40 g total mass using 100 watt lamp
[b]= cell containing 0.60 g total mass using 400 watt lamp

COMPARATIVE EXAMPLES

A series of experiments similar to those of Examples 1 to 5 were carried out with trans-methyl 2-(2,2-dichlorovinyl)-3,3-di-methylcyclopropane-carboxylate (Compound A) and with trans-2-(2,2-dichlorovinyl)-3,3-dimethylcyclopropanecarboxylic acid (Compound B) instead of trans-DCVN. The yields of the corresponding cis-compounds at the photostationary state are given in Table II, alongiside—for convenience of cross-reference—the yields obtained according to the invention as illustrated in Examples 1 to 5.

TABLE II

| Sensitizer | Yield of cis-compound at photostationary state (%) | | |
|---|---|---|---|
| | cis-DCVN | cis-Compound A | cis-Compound B[1] |
| Aceto-phenone | 63.0 (Example 1) | 33.0 | 32.0 |
| Propio-phenone | 62.5 (Example 2) | 35.0 | — |
| Iso-Butyro-phenone | 62.0 (Example 4) | 36.0 | — |
| Benzo-phenone | 62.5 (Example 5) | 35.0 | 32.0 |

[1]as a homogeneous solution of Compound B and the photosensitiser could not be achieved, ethanol had to be used as solvent the mixture being 50% ethanol, 20% photosensitiser, 30% Compound B by weight.

It will be seen from the results of the comparative experiments that the use of DCVN as opposed to the use of the free acid (Compound B) or its methyl ester (Compound A) results in a trans-to-cis conversion dramatically higher than the maximum yield achievable with the free acid or its methyl ester.

I claim:

1. A process for the conversion of a trans-cyclopropane-nitrile of the following general formula

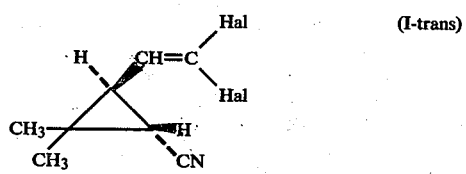

(I-trans)

to the corresponding cis-compound, wherein each Hal is a halogen atom, comprising:
  irradiating the trans-compound (I-trans) with light of wave-length in the range 260 to 450 nanometers in the presence of a photosensitizer the triplet state energy of which is in the range 220 to 330 kilojoules per mole.

2. The process as in claim 1 wherein said Hal is chlorine.

3. The process as in claim 1 wherein said Hal is bromine.

4. The process as in claim 1 wherein said photo-sensitizer is a diaryl ketone.

5. The process as in claim 1 wherein said photosensitizer is an alkyl aryl ketone.

6. The process as in claim 1 wherein the amount of photosensitizer present is in the range 5% to 40% by weight of the nitrile.

7. The process as in claim 1 carried out in the absence of oxygen.

8. The process as in claim 1, wherein the wave length of light is in the range of 280 to 400 nanometers.

9. The process as in claim 1, wherein the triplet state energy of the photo-sensitizer is in the range of 250 to 310 kilojoules per mole.

* * * * *

UNITED STATES PATENT AND TRADEMARK OFFICE
CERTIFICATE OF CORRECTION

PATENT NO. : 4,421,618

DATED : December 20, 1983

INVENTOR(S) : Kingsley Salisbury

It is certified that error appears in the above-identified patent and that said Letters Patent are hereby corrected as shown below:

In the Abstract, Last Line, please delete "220-230" and insert therefor -- 220-330 --.

In Column 1, The Title, please delete "photoisomerization" and insert therefor -- photoisomerisation --.

In Column 1, Line 25, please delete "2,2-di-chlorovinyl)" and insert therefor -- (2,2-di-chlorovinyl) --.

In Column 1, Line 30, please delete "-ismoers;" and insert therefor -- -isomers; --.

In Column 2, Line 20, please delete "so-caled" and insert therefor -- so-called --.

In Column 3, Line 26, please delete "fron" and insert therefor -- from --.

In Column 3, Line 29, please delete "measurements.were" and insert therefor -- measurements were --.

UNITED STATES PATENT AND TRADEMARK OFFICE
CERTIFICATE OF CORRECTION

PATENT NO. : 4,421,618        Page 2 of 2
DATED : December 20, 1983
INVENTOR(S) : Kingsley Salisbury It is certified that error appears in the above-identified patent and that said Letters Patent is hereby corrected as shown below:

In Table I, The Title of the Far Right Column, please delete "Yield of cis-DCVN at Photo-stationary state" and insert therefor -- Yield of cis-DCVN at Photo-stationary state % --

Signed and Sealed this

First Day of May 1984

[SEAL]

Attest:

GERALD J. MOSSINGHOFF

*Attesting Officer*     *Commissioner of Patents and Trademarks*